United States Patent [19]

Huebner

[11] 4,076,600
[45] Feb. 28, 1978

[54] LEVELING AGENT FOR ACID ZINC ELECTROPLATING BATHS AND METHOD

[75] Inventor: Karen Huebner, Parma, Ohio

[73] Assignee: R. O. Hull & Company, Inc., Cleveland, Ohio

[21] Appl. No.: 752,079

[22] Filed: Dec. 20, 1976

[51] Int. Cl.² .............................................. C25D 3/22
[52] U.S. Cl. ........................... 204/55 R; 204/DIG. 2; 252/182
[58] Field of Search ................. 204/55 R, 55 Y, 43 Z, 204/44, 114, DIG. 2; 252/182

[56] References Cited
U.S. PATENT DOCUMENTS 3,884,774  5/1975  Kessler .............................. 204/55 Y Primary Examiner—G. L. Kaplan
Attorney, Agent, or Firm—Armand P. Boisselle

[57] ABSTRACT

An aqueous plating bath for the electrodeposition of a zinc coating on a substrate is disclosed and comprises zinc ions, and an amount, sufficient to provide a level zinc electrodeposit, of one or more bath-soluble leveling phosphorus cations having the formula:

$$R_4P^{\oplus}$$

wherein each R is independently a hydroxy alkyl group. Baths are also described which contain, in addition to the phosphorus cations identified above, at least one nitrogen-containing compound obtained by reacting (a) ammonia, an aliphatic amine containing at least one primary amine group, or mixtures of two or more of any of these with (b) one or more epihalohydrins, glycerol halohydrins, or mixtures thereof, and at least one thiourea having the general formula:

$$[R'_2N]_2CS$$

wherein each R' is independently hydrogen or an alkyl or alkenyl group. Methods for electrodeposition of level zinc deposits from such baths and additive compositions for preparing and maintaining the baths are disclosed.

66 Claims, No Drawings

LEVELING AGENT FOR ACID ZINC ELECTROPLATING BATHS AND METHOD

BACKGROUND OF THE INVENTION

This invention relates to the electrodeposition of zinc, and particularly to a plating bath for plating bright, level zinc deposits from aqueous acid plating baths. More particularly, the improvement relates to incorporation in the bath of a phosphorus cation having the formula:

$$R_4P^{\oplus}$$

wherein each R is independently a hydroxy alkyl group. The invention also relates to methods for electrodeposition of level zinc deposits from such baths and to additive compositions for preparing and maintaining the baths.

Considerable attention has been directed to the development of zinc electroplating baths which will produce bright and level zinc deposits of improved quality. Research has been devoted to improving the overall brightness, the range of allowable current densities, and the ductility of the zinc deposit with alkaline zinc baths dominating the field of zinc electroplating for many years due primarily to the heretofore unsolved problems accompanying the use of acid zinc baths specified above. Until recently, most of the successful aqueous alkaline zinc plating baths have contained substantial quantities of cyanide which has caused concern regarding toxicity and waste disposal problems.

The enactment and enforcement of the various environmental protection laws, especially those designed to improve water quality, have increased the pressures on the industry to reduce or eliminate the use and discharge of baths containing cyanides. As a result, increased efforts to develop bright zinc plating processes to replace the classical zinc cyanide baths has been increased.

Typically, acid plating baths have been based on a suitable inorganic zinc salt such as zinc sulfate, zinc cloride, zinc fluoborate, zinc acetate, zinc sulfamate, or zinc pyrophosphate. The bath usually includes a buffer such as the corresponding ammonium salt and other additives to promote and improve ductility, brightness, throwing power and covering power. Surface active agents may be included to improve the crystal structure, reduce pitting, and increase the solubility of the other additives.

SUMMARY OF THE INVENTION

The present invention relates to the discovery that a bright and level zinc electrodeposit can be obtained from aqueous acid plating baths containing zinc ions and an amount, sufficient to provide a level zinc electrodeposit, of one or more bath-soluble leveling phosphorus cations having the general formula:

$$R_4P^{\oplus}$$

wherein each R is independently a hydroxy alkyl group. The present invention also comprises methods for the electrodeposition of bright and level zinc deposits from such baths as well as additive compositions for forming aqueous acid zinc plating baths.

DESCRIPTION OF THE PREFERRED EMBODIMENTS

The compositions of the invention which are particularly useful as leveling agents for the aqueous acidic plating baths of the invention are characterized by the following formula:

Formula I $$R_4P^{\oplus}$$

wherein each R is independently a hydroxyl alkyl group such as $R''CH(OH)-$ and $HOR'''-$ wherein $R''$ is hydrogen or a lower alkyl group containing, for example, from about 1 to 10 or 15 carbon atoms and $R'''$ is an alkylene group containing from about 1 to 10 carbon atoms. The alkyl and alkylene groups may be straight chain or branched groups.

The preferred phosphorus cation has a general formula:

Formula II $$R''CH(OH)_4P^{\oplus}$$

wherein $R''$ is as defined above. The phosphorus cation may be prepared by the reaction of phosphine with an aldehyde ($R''CHO$) and a mineral acid in an inert solvent such as tetrahydrofuran. This procedure is described in detail in U.S. Pat. No. 3,013,085 which is incorporated herein by reference. The product obtained in this manner is a phosphonium salt having the formula:

$$[R''CH(OH)]_4P^{\oplus} X^{\ominus}$$

wherein $X^{\ominus}$ is the anion of the acid utilized in the reaction.

Typical examples of such phosphonium salts include those where $R''$ is $n-C_5H_{11}$, $n-C_3H_7$ or H, and X is bromine, iodine, formate, acetate, benzoate, etc. The anion X also may be hydroxy anion obtained by hydrolysis of the corresponding halide. The anion is not critical to the invention so long as the anion is one which does not deleteriously affect the performance of the bath. For example, oxidizing anions such as $NO_3^{\ominus}$ should be avoided in the acid zinc baths of the invention. The phosphorus leveling compounds utilized in the acid plating baths of the invention generally are prepared and added to the plating baths as phosphonium salts and the anion is preferably a halide. Typical examples of the phosphonium salts include tetrakis(hydroxymethyl)phosphonium chloride, tetrakis(1-hydroxyethyl)phosphonium chloride, tetrakis(1-hydroxypentyl)phosphonium iodide, and tetrakis(1-hydroxypropyl)phosphonium chloride.

The above-identified phosphorus cations are effective leveling agents in conventional aqueous acidic zinc plating baths which are known to those skilled in the art. Such baths contain free zinc ions and are prepared with zinc sulfate, zinc chloride, zinc fluoroborate and-/or zinc sulphamate. The zinc plating baths normally will contain conducting salts and boric acid. Examples of conductive salts utilized in the acid zinc plating baths of the invention include sodium chloride, sodium fluoride, ammonium fluoride, ammonium chloride, etc. The acid zinc plating baths which are improved in accordance with this invention by the incorporation of the phosphorus cations described above also may contain other additives such as conventional brighteners, wetting agents, etc.

The acidic zinc electroplating baths of the invention may be utilized to produce zinc deposits on all types of metals and alloys, for example, on iron, zinc die cast, copper and brass, and the phosphorus cations of the invention may be added to zinc plating baths employed in all types of industrial zinc plating processes including still plating baths, high-speed plating baths for strip or wire plating, and in barrel plating.

The amount of the above-described phosphorus cation which is added to the acidic zinc electroplating baths of the invention is an amount sufficient to produce a level zinc deposit on the substrate and generally may range from about 0.001 to about ten grams per liter of bath and preferably from about 0.01 to about four grams per liter of bath.

Boric acid which is normally included in the zinc plating baths of the invention serves as a weak buffer to control the pH and the cathode film. The boric acid also is helpful in smoothing the deposit and is believed to have a cooperative effect with the leveling agents of the invention. The concentration of boric acid in the bath is not critical and generally will be in the range of from about 30 to about 60 grams per liter. The inorganic salts of zinc such as zinc sulfate heptahydrate may be present in the plating baths of the invention in amounts ranging from about 300 to about 600 grams per liter. The conductive salts such as ammonium or sodium fluoride, ammonium or sodium chloride, etc., are present in amounts ranging from about ten to about 30 grams per liter or more.

The properties of the zinc deposited by the baths of the invention may be enhanced further by including in the bath a small amount such as from about 0.5 to about four grams per liter of a nitrogen-containing compound obtained by reacting (a) ammonia, an aliphatic amine containing at least one primary amine group, or mixtures of two or more of any of these with (b) one or more epihalohydrins, glycerol halohydrins, or mixtures thereof. Examples of aliphatic amines which are useful for preparing these compounds include the aliphatic acyclic amines such as methylamine, ethylamine, propylamine, butylamine, etc., and alkylene polyamines having the general formula:

Formula III

H$_2$N—alkylene NH)$_x$ alkylene NH$_2$ wherein $x$ is an integer from zero to four and the alkylene may be a straight or branched chain group containing up to about six carbon atoms. Examples of such alkylene polyamines containing at least one primary amine group include ethylene diamine, triethylamine tetramine, propylene diamine, N-ethyl-ethylene diamine, tripropylene tetramine, tetraethylene pentamine and pentaethylene hexamine. Combinations of ammonia with one or more of the aliphatic amines can be reacted with the epoxy compound as well as combinates of the aliphatic acyclic amines. Alternatively, the reaction product of ammonia with an epoxy compound can be added to a plating bath along with a reaction product of an amine with an epoxy compound of formulas IV and V.

The epihalohydrins that may be reacted with the ammonia and/or aliphatic amines include epihalohydrins and derivatives of epihalohydrins having the formula Formula IV

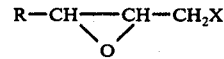

wherein X is halogen and R is hydrogen or a lower alkyl radical. Examples of such compounds include epichlorohydrin, epibromohydrin and 1-chloro-2,3-epoxybutane. Epichlorohydrin is preferred. Other compounds having similar reactivity to the epihalohydrins, such as glycerol halohydrins, having the following formula may be utilized:

Formula V

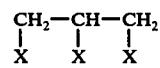

wherein at least one but not more than two of the X's are hydroxy groups and the remaining X's are chlorine or bromine. Examples of such reactants include, for example, 1,3-dichloro-2-hydroxypropane, 3-chloro-1,2-dihydroxypropane, and 2,3-dichloro-1-hydroxypropane.

The nitrogen-containing compound utilized in the baths of the invention may be prepared in accordance with the methods described in U.S. Pat. No. 2,791,554, and the disclosure of that patent is hereby incorporated by reference. Various ratios of the ingredients may be selected although it is preferred generally to react ammonia of aliphatic amines containing containing one primary amine group with epihalohydrin or glycerol halohydrin in a molar ratio of at least 2:1. The reaction between aliphatic amines containing two primary amine groups such as ethylene diamine with epihalohydrin or glycerol halohydrin normally is conducted with molar ratios of at least about 1:1 and ratios of about up to 2:1 have been found to be particularly useful. More specifically, the nitrogen-containing compounds utilized in the invention are prepared by mixing the ammonia or amine compound with water in a reaction vessel followed by the addition of the epihalohydrin or glycerol halohydrin while maintaining the reaction temperature below about 60° C.

In addition to the above-described ingredients, the acid zinc plating baths of the invention also may contain at least one thiourea compound having the formula

[R'$_2$N]$_2$CS wherein each R' is independently hydrogen or an alkyl or alkenyl radical. The amount of thiourea compound incorporated into the plating baths of the invention may vary from about 0.01 to about one gram per liter. In addition to thiourea, the substituted thioureas of the type included within the above formula are available commercially and include, for example, allyl thiourea, N,N'-di-n-butyl thiourea, sym-diethyl urea, and 1,1,3,3-tetraethyl-2-thiourea. Zinc plating baths containing at least one or more of each of the above-described phosphorus cations, the nitrogen-containing compounds and the thiourea compounds have been found to be particularly effective.

The acidic zinc plating baths of the present invention deposit a level zinc deposit on substrates at any conventional temperature such as from about 25° to about 60° C. Still plating baths generally will be operated at a lower range of the temperature such as from about 25° to about 40° C., whereas high-speed plating baths for strip or wire plating may be operated over the entire range of 25° to about 60° C. The acidity of the bath may vary from a pH of from about 1.5 to about 6 or 7. The pH may be lowered if desired by the addition of acid solutions, such as a 10% sulfuric acid solution. If the pH falls below the desired operating range, it may be increased by the addition of ammonium hydroxide.

Two typical acidic zinc plating baths to which the additive compositions of the invention may be illustrated as follows:

| Bath #1 | |
|---|---|
| $ZnSO_4 H_2O$ | 267 g/l |
| NaCl | 15 g/l |
| $H_3BO_3$ | 15 g/l |
| pH | 2.6 |

In the following specific examples, the utility of the invention is demonstrated by plating steel Hull cell panels in a 267ml Hull cell. Current densities were measured with a Hull cell scale. The panels were plated at .5 amperes for 5 minutes from a D.C. rectifier. The solutions were mechanically agitated.

EXAMPLE I

Bath #1 to which is added:
0.2g/l of the reaction product of ammonia and epichlorohydrin (mole ratio 2:1)
0.3g/l thiourea
0.6g/l tetrakis(hydroxymethyl)phosphonium chloride (THPC)
Result: Bright to semibright, level, zinc plate above 20 asf.

EXAMPLE II

Bath #1 to which is added:
0.2g/l of the reaction product of ammonia and epichlorohydrin (mole ratio 2:1)
0.30g/l thiourea
0.6g/l THPC
1.0g/l of the reaction product of ethylene diamine and epichlorohydrin (mole ratio 1:1)
Result: Bright level plate above 50 asf.

EXAMPLE III

Bath #2 to which is added:
2g/l of the reaction product of ethylene diamine and epichlorohydrin (mole ratio 1:1)
0.6g/l THPC
0.3g/l thiourea
Result: Bright level deposit above 10 asf.

EXAMPLE IV

Bath #1 to which is added:
0.1g/l of the reaction product of ammonia and epichlorohydrin (mole ratio of 2:1)
1.0g/l ethylene diamine : epichlorohydrin (mole ratio 1:1)
0.6g/l THPC
0.3g/l methyl-3-hydroxyethyl thiourea
Result: Bright level deposit above 75 asf.

In practice, the improved zinc plating baths containing the phosphorus cations of the invention and other additives may be operated on a continuous or intermittent basis, and from time to time, the components of the bath have to be replenished. The various components may be added singularly as required or may be added in combination. The amounts of the various additive compositions to be added to the plating baths may be varied over a wide range depending on the nature and performance of the zinc plating bath to which the composition is added. Such amounts can be determined readily by one skilled in the art.

Another aspect of this invention relates to additive compositions which may be mixtures of the compositions without any solvent or carrier or they may be concentrates of bath components in water, alcohols (e.g., propanol), or mixtures of water and one or more alcohols. The additive compositions will comprise the phosphorus cation according to Formula I and one or more of the additional bath components described above such as the nitrogen-containing compounds and the thioureas. The amounts of the compounds in the additive compositions or concentrates will be such tht when they are diluted, they will provide the requisite amounts of the components in the bath or to replenish the bath.

The following additive compositions or concentrates illustrate the various combinations of compounds that may be prepared and utilized in accordance with the invention for preparing or maintaining the baths of the invention and/or improving the performance of the baths of the invention.

| | Parts by Weight |
|---|---|
| Additive Composition 1 | |
| Tetrakis(hydroxymethyl)phosphonium chloride | 6.0 |
| Thiourea | 3.1 |
| Additive Composition 2 | |
| Tetrakis(hydroxymethyl)phosphonium chloride | 6.0 |
| Thiourea | 3.1 |
| Reaction product of ammonia and epichlorohydrin (1:1) | 10.0 |
| Additive Composition 3 | |
| Tetrakis(hydroxymethyl)phosphonium chloride | 12.0 |
| Reaction product of ethylene diamine with epichlorohydrin (1:2.2) | 15.0 |
| Water | 73.0 |
| Additive Composition 4 | |
| Tetrakis(hydroxyethyl)phosphonium hydroxide | 10.0 |
| Allyl thiourea | 5.0 |
| Propanol | 5.0 |
| Additive Composition 5 | |
| Tetrakis(2-hydroxyethyl)phosphonium chloride | 6.0 |
| Thiourea | 3.0 |
| Additive Composition 6 | |
| Tetrakis(2-hydroxyethyl)phosphonium chloride | 6.0 |
| Thiourea | 3.0 |
| Ethyl alcohol | 10.0 |

The embodiments of the invention in which an exclusive property or privilege is claimed are defined as follows:

1. An aqueous acidic plating bath for the electrodeposition of a zinc coating on a substrate which comprises zinc ions, and an amount, sufficient to provide a level zinc electrodeposit, of one or more bath-soluble leveling phosphorus cations having the formula:

$$R_4P^{\oplus}$$

wherein each R is independently a hydroxy alkyl group.

2. The plating bath of claim 1 wherein each R is the hydroxy methyl group.

3. The plating bath of claim 1 wherein the bath also contains at least one nitrogen-containing compound obtained by reacting (a) ammonia, an aliphatic amine containing at least one primary amine group, or mixtures of two or more of any of these with (b) one or more epihalohydrins, glycerol halohydrins, or mixtures thereof.

4. The plating bath of claim 3 wherein the nitrogen-containing compound is obtained by reacting ammonia with epichlorohydrin.

5. The plating bath of claim 4 wherein the molar ratio of ammonia and epichlorohydrin is at least about 2:1.

6. The plating bath of claim 5 wherein the ammonia and epichlorohydrin are reacted in the presence of water at a temperature below about 60° C.

7. The plating bath of claim 3 wherein the nitrogen-containing compound is obtained by reacting ethylene diamine with epichlorohydrin.

8. The plating bath of claim 7 wherein the molar ratio of ethylene diamine and epichlorohydrin is at least about 1:1.

9. The plating bath of claim 7 wherein the ethylene diamine and epichlorohydrin are reacted in the presence of water at a temperature below about 60° C.

10. The plating bath of claim 3 also containing at least one thiourea having the general formula:

$$[R'_2N]_2CH$$

wherein each R' is independently hydrogen or an alkyl or alkenyl group.

11. The plating bath of claim 10 wherein R' is hydrogen.

12. The plating bath of claim 3 wherein (a) and (b) are reacted in the presence of water at a temperature below about 60° C.

13. An aqueous acidic plating bath for the electrodeposition of a zinc coating on a substrate which comprises zinc ions and an amount, sufficient to provide a level zinc electrodeposit, of one or more bath-soluble phosphorus cations having the general formula:

$$[R''CH(OH)_4]P^{\oplus}$$

wherein each R'' is independently hydrogen or a lower alkyl group.

14. The plating bath of claim 13 wherein R'' is hydrogen.

15. The plating bath of claim 13 wherein the bath also contains at least one nitrogen-containing compound obtained by reacting (a) ammonia, an aliphatic amine containing at least one primary amine group or mixtures of two or more of any of these, with (b) one or more epihalohydrins, glycerol halohydrins, or mixtures thereof.

16. The plating bath of claim 15 wherein the nitrogen-containing compound is obtained by reacting ammonia with epichlorohydrin.

17. The plating bath of claim 16 wherein the molar ratio of ammonia and epichlorohydrin is about at least 2:1.

18. The plating bath of claim 17 wherein the ammonia and epichlorohydrin are reacted in the presence of water at a temperature, below about 60° C.

19. The pating bath of claim 15 wherein the nitrogen-containing compound is obtained by reacting ethylene diamine with epichlorohydrin.

20. The plating bath of claim 19 wherein the molar ratio of ethylene diamine and epichlorohydrin is at least about 1:1.

21. The plating bath of claim 20 wherein the ethylene diamine and epichlorohydrin are reacted in the presence of water at a temperature below about 60° C.

22. The plating bath of claim 15 also containing at least one thiourea having the general formula:

$$[R'_2N]_2CS$$

wherein each R' is independently hydrogen, an alkyl, or an alkenyl group.

23. The plating bath of claim 22 wherein R' is hydrogen.

24. The plating bath of claim 15 wherein (a) and (b) are reacted in the presence of water at a temperature below about 60° C.

25. The method of electrodepositing a zinc coating on a substrate which comprises electroplating said substrate in an aqueous acidic bath which comprises zinc ions, and an amount, sufficient to provide a level zinc electrodeposit, of one or more bath-soluble leveling phosphorus cations having the formula:

$$R_4P^{\oplus}$$

wherein each R is independently a hydroxy alkyl group.

26. The method of claim 25 wherein each R is the hydroxy methyl group.

27. The method of claim 25 wherein the bath also contains at least one nitrogen-containing compound obtained by reacting (a) ammonia, an aliphatic amine containing at least one primary amine group, or mixtures of two or more of any of these with (b) one or more epihalohydrins, glycerol halohydrins, or mixtures thereof.

28. The method of claim 27 wherein the nitrogen-containing compound is obtained by reacting ammonia with epichlorohydrin.

29. The method of claim 28 wherein the molar ratio of ammonia and epichlorohydrin is at least about 2:1.

30. The method of claim 29 wherein the ammonia and epichlorohydrin are reacted in the presence of water at a temperature below about 60° C.

31. The method of claim 27 wherein the nitrogen-containing compound is obtained by reacting ethylene diamine with epichlorohydrin.

32. The method of claim 31 wherein the molar ratio of ethylene diamine and epichlorohydrin is at least about 1:1.

33. The method of claim 32 wherein the ethylene diamine and epichlorohydrin are reacted in the presence of water at a temperature below about 60° C.

34. The method of claim 27 also containing at least one thiourea having the general formula:

$$[R'_2N]_2CS$$

wherein each R' is independently hydrogen or an alkyl or alkenyl group.

35. The method of claim 26 wherein R' is hydrogen.

36. The method of claim 27 wherein (a) and (b) are reacted in the presence of water at a temperature below about 60° C.

37. The method of electrodepositing a zinc coating on a substrate which comprises electroplating the substrate in an aqueous acidic bath which comprises zinc ions and an amount, sufficient to provide a level zinc electrodeposit, of one or more bath-soluble phosphorus cations having the general formula:

$$[R''(CH(OH)]_4 P^{\oplus}$$

wherein each R'' is independently hydrogen or a lower alkyl group.

38. The method of claim 37 wherein R'' is hydrogen.

39. The method of claim 38 wherein the bath contains from about 0.1 to about four grams of the phosphorus cation per liter of bath.

40. The method of claim 37 wherein the bath also contains at least one nitrogen-containing compound obtained by reacting (a) ammonia, an aliphatic amine containing at least one primary amine group or mixtures of two or more of any of these, with (b) one or more epihalohydrins, glycerol halohydrins, or mixtures thereof.

41. The method of claim 40 wherein the nitrogen-containing compound is obtained by reacting ammonia with epichlorohydrin.

42. The method of claim 41 wherein the molar ratio of ammonia and epichlorohydrin is about at least 2:1.

43. The method of claim 42 wherein the ammonia and epichlorohydrin are reacted in the presence of water at a temperature below about 60° C.

44. The method of claim 40 wherein the nitrogen-containing compound is obtained by reacting ethylene diamine with epichlorohydrin.

45. The method of claim 44 wherein the molar ratio of ethylene diamine and epichlorohydrin is at least about 1:1.

46. The method of claim 45 wherein the ethylene diamine and epichlorohydrin are reacted in the presence of water at a temperature below about 60° C.

47. The method of claim 40 also containing at least one thiourea having the general formula:

$$[R'_2 N]_2 CS$$

wherein each R' is independently hydrogen, an alkyl, or an alkenyl group.

48. The method of claim 47 wherein R' is hydrogen.

49. The method of claim 40 wherein (a) and (b) are reacted in the presence of water at a temperature below about 60° C.

50. An additive composition for an aqueous acidic zinc electroplating bath comprising a mixture of
a. one or more bath-soluble phosphorus cations having the formula $$R_4 P^{\oplus}$$

wherein each R is independently a hydroxy alkyl group, and
b. at least one thiourea having the formula $$[R'_2 N]_2 CS$$

wherein each R' is independently hydrogen or an alkyl or alkenyl group.

51. The additive composition of claim 50 wherein R is [R''CHOH] wherein R'' is hydrogen or a lower alkyl group.

52. The additive composition of claim 51 wherein R'' is hydrogen.

53. The additive composition of claim 50 wherein R' is hydrogen.

54. The additive composition of claim 50 wherein the mixture also contains (c) at least one nitrogen-containing compound obtained by reacting ammonia with one or more epihalohydrins, glycerol halohydrins, or mixtures thereof.

55. The additive composition of claim 54 wherein the nitrogen-containing compound is obtained by reacting ammonia with epichlorohydrin in a molar ratio of at least 2:1.

56. The additive composition of claim 55 wherein the nitrogen-containing compound is obtained by reacting ammonia with epichlorohydrin in the presence of water at a temperature below about 60° C.

57. The additive composition of claim 54 wherein the nitrogen-containing compound is obtained by reacting ammonia with one or more epichlorohydrins, glycerol halohydrins, or mixtures thereof in the presence of water at a temperature below about 60° C.

58. An additive composition for an aqueous acidic zinc electroplating bath comprising a mixture of
a. one or more bath-soluble phosphorus cations having the formula $$R_4 P^{\oplus}$$

wherein each R is independently a hydroxy alkyl group, and
b. at least one nitrogen-containing compound obtained by reacting
  i. ammonia, an aliphatic amine containing at least one primary amine group, or mixtures of two or more of any of these with
  ii. one or more epihalohydrins, glycerol halohydrins or mixtures thereof.

59. The additive composition of claim 58 wherein R is [R''CHOH] wherein R'' is hydrogen or a lower alkyl group.

60. The additive composition of claim 59 wherein R'' is hydrogen.

61. The additive composition of claim 58 wherein the nitrogen-containing compound is obtained by reacting ammonia with epichlorohydrin in a molar ratio of at least about 2:1.

62. The additive composition of claim 61 wherein the nigrogen-containing compound is obtained by reacting ammonia with epichlorohydrin in the presence of water at a temperature below about 60° C.

63. The additive composition of claim 58 wherein the nitrogen-containing compound is obtained by reacting ethylene diamine with epichlorohydrin.

64. The additive composition of claim 63 wherein the molar ratio of ethylene diamine and epichlorohydrin is at least about 1:1.

65. The additive composition of claim 64 wherein the ethylene diamine and epichlorohydrin are reacted in the presence of water at a temperature below about 60° C.

66. The additive composition of claim 58 wherein the nitrogen-containing compound (b) is obtained by reacting (i) and (ii) in the presence of water at a temperature below about 60° C.

* * * * *

UNITED STATES PATENT AND TRADEMARK OFFICE
CERTIFICATE OF CORRECTION

PATENT NO. : 4,076,600
DATED : February 28, 1978
INVENTOR(S) : Karen Huebner

It is certified that error appears in the above—identified patent and that said Letters Patent is hereby corrected as shown below:

Column 5, line 26, insert the following:

Bath #2

| | |
|---|---|
| $ZnSO_4H_2O$ | 150g/1 |
| $Na_2SO_4$ | 45g/1 |
| NaCl | 15g/1 |
| $H_3BO_3$ | 20g/1 |
| pH | 4.5 |

In claim 10, the formula should read:

$$[R'_2N]_2CS$$

Signed and Sealed this
Second Day of June 1981

[SEAL]

Attest:

RENE D. TEGTMEYER

Attesting Officer

Acting Commissioner of Patents and Trademar